United States Patent [19]

Iwasaki et al.

[11] Patent Number: 5,500,484
[45] Date of Patent: Mar. 19, 1996

[54] 2-ALKOXY- OR ACYLOXY-2-ARYL-1,3-PROPANEDIOL OR DIOXANE DERIVATIVE, AND PROCESS FOR ITS PRODUCTION

[75] Inventors: Hideharu Iwasaki, Ibaraki; Koichi Yoneda, Chiba; Yoichi Kido, Ibaraki; Takeo Hosogai, Saitama; Kazuo Itoi, Okayama; Masahiko Kitayama, Ibaraki, all of Japan

[73] Assignee: Kuraray Co., Ltd., Kurashiki, Japan

[21] Appl. No.: 297,112

[22] Filed: Aug. 26, 1994

[30] Foreign Application Priority Data

| Aug. 26, 1993 | [JP] | Japan | 5-234242 |
| Aug. 26, 1993 | [JP] | Japan | 5-234243 |
| Nov. 8, 1993 | [JP] | Japan | 5-302401 |
| Nov. 30, 1993 | [JP] | Japan | 5-326161 |
| Nov. 30, 1993 | [JP] | Japan | 5-326162 |

[51] Int. Cl.$^6$ .................................................. C07C 43/13
[52] U.S. Cl. .......................... 568/660; 568/662; 549/502; 549/78; 549/372
[58] Field of Search ........................... 568/660, 662; 549/502, 78

[56] References Cited

U.S. PATENT DOCUMENTS 5,072,056  12/1991  Stiefel .

OTHER PUBLICATIONS

Chemical Abstracts, vol. 84, No. 3, Jan. 19, 1976, AN 16636g, p. 402.
J. Med. Chem., 1992, No. 14, vol. 35, pp. 2600–2609, Graham C. Crawley, et al., "Methoxytetrahydropyrans. A New Series of Selective and Orally Potent 5-Lipoxygenase Inhibitors".
Tetrahedron, vol. 46, No. 20, pp. 7081–7092, 1990, Giuseppe Guanti, et al., "Enzyme Catalyzed Monohydrolysis of 2–aryl–1,3–propanediol Diacetates. A Study of Structural Effects of the Aryl Moiety on the Enantioselectivity".
Synthesis, No. 4, 1981, pp. 280–282, George A. Olah, et al., "Synthetic Methods and Reactions; 68$^1$. Nafion–H–Catalyzed Hydration and Methanolysis of Epoxides".
Chemical Abstracts, Chemical Substances, Eleventh Collective Index, vol. 96–105, 1982–1986, p. 54250.
J. Org. Chem., vol. 52, No. 12, 1987, pp. 2559–2562, Pier Lucio Anelli, et al., "Fast and Selective Oxidation of Primary Alcohols to Aldehydes or to Carboxylic Acids and of Secondary Alcohols to Ketones Medicated by Oxoammonium Salts under Two-Phase Conditions".
Chemical Abstracts, vol. 111, No. 19, Nov. 6, 1989, AN 174025n, p. 718.
Journal of the American Chemical Society, vol. 90, No. 13, Jun. 19, 1968, pp. 3444–3458, Ernest L. Eliel, et al., "Conformational Analysis. XVI. 1,3–Dioxanes$^{1,2}$".
Tetrahedron Letters, vol. 27, No. 33, pp. 3935–3938, 1986, E. Ghera, et al., "Synthesis of Maturone".
Tetrahedron Letters, vol. 28, No. 11, pp. 1195–1198, 1987, Alan R. Katritzky, et al., "Acetals and Ketals of 2–(2–pyridyl)propane–1,3–diol Novel Protection for Carbonyl Groups".
Chemical Abstracts, Chemical Substances, Twelfth Collective Index, vol. 106–115, 1987–1991, p. 32557.

Primary Examiner—Nicky Chan
Attorney, Agent, or Firm—Oblon, Spivak, McClelland, Maier & Neustadt

[57] ABSTRACT

A compound that can be converted, at a low cost and in a simple way, into 2-aryl-1,3-propanediols serving as precursors for synthesizing felbamate acting as an antiepileptic has a structure represented by Formula (1):

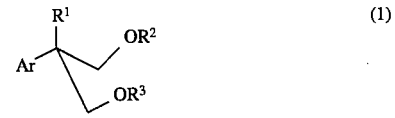

wherein Ar represents an aryl group; $R^1$ represents a hydrogen atom or is $R^4$ or $R^5$, where $R^4$ represents an alkoxy group having 1 to 10 carbon atoms and $R^5$ represents a hydroxy group or an acyloxy group having 1 to 10 carbon atoms; and $R^2$ and $R^3$ are hydrogen atoms at the same time or $R^2$ and $R^3$ together form a group represented by Formula (2):
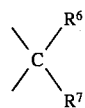
(2)
wherein $R^6$ and $R^7$ each independently represent a hydrogen atom or an alkyl group having 1 to 5 carbon atoms, or $R^6$ and $R^7$ together form an oligomethylene group having 2 to 10 carbon atoms.
1 Claim, No Drawings

2-ALKOXY- OR ACYLOXY-2-ARYL-1,3-PROPANEDIOL OR DIOXANE DERIVATIVE, AND PROCESS FOR ITS PRODUCTION

BACKGROUND OF THE INVENTION

1. Field of the Invention

This invention relates to a novel 2-alkoxy- or acyloxy-2-aryl-1,3-propanediol or dioxane derivative from which a 2-aryl-1,3-propanediol, a precursor or intermediate for synthesizing physiologically active substances such as felbamate of the formula (A):

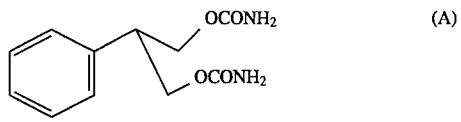 (A)

that acts as an antiepileptic, can be derived in a high yield, and a process for producing the same. The present invention also relates to a process for producing a 2-aryl-1,3-propanediol obtained from that derivative, and a process for producing a glycol monoether that can serve as a starting material for synthesizing the derivative.

2. Description of the Related Art

Hitherto, 2-aryl-1,3-propanediols are produced by a process in which an aryl-substituted malonate is reduced, a process in which a 2-nitro-2-aryl-1,3-propanediol is subjected to catalytic hydrogenation, or a process in which an ester of 1-hydroxymethyl-1-phenyl acetic acid is reduced.

As the above process for producing 2-aryl-1,3-propanediols by reducing malonates, specifically a process in which an expensive metal hydride reducing agent such as lithium aluminum hydride is used in a stoichiometric amount [U.S. Pat. Nos. 5,091,595 and 4,982,016 and J. Org. Chem., 54, 1198 (1989)] and a process in which hydrogenation is carried out in the presence of copper chromite catalyst under application of a pressure of as high as 5,000 p.s.i. [J. Am. Chem. Soc., 70, 3121 (1948)] are known in the art.

These processes, however, have economical and operational difficulties from the viewpoint of their application in an industrial scale, and have room for greater improvements.

The process in which a 2-nitro-2-aryl-1,3-propanediol is subjected to catalytic hydrogenation (U.S. Pat. Nos. 5,072,056 and 4,868,327) has the problem that nitroalkane derivatives full of danger of explosion must be handled.

The process in which an ester of 1-hydroxymethyl-1-phenyl acetic acid is reduced (U.S. Pat. No. 5,239,121) also has the problems that the ester of 1-hydroxymethyl-1-phenyl acetic acid itself may readily undergo dehydration to form an active acrylic acid derivative and that expensive metal hydride reducing agents must be used.

SUMMARY OF THE INVENTION

An object of the present invention is to provide a compound that can be safely and readily converted into 2-aryl-1,3-propanediols serving as precursors for synthesizing felbamate, and a process for producing an intermediate for synthesizing the compound.

The present invention provides a novel 2-alkoxy- or acyloxy-2-aryl-1,3-propanediol or dioxane derivative represented by Formula (1):

 (1)

wherein Ar represents an aryl group; $R^1$ represents a hydrogen atom or is $R^4$ or $R^5$ where $R^4$ represents an alkoxy group having 1 to 10 carbon atoms and $R^5$ represents a hydroxy group or an acyloxy group having 1 to 10 carbon atoms; and $R^2$ and $R^3$ are hydrogen atoms at the same time or $R^2$ and $R^3$ together form a group represented by Formula (2):

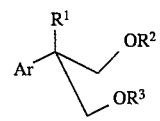 (2)

wherein $R^6$ and $R^7$ each independently represent a hydrogen atom or an alkyl group having 1 to 5 carbon atoms, or $R^6$ and $R^7$ together form an oligomethylene group having 2 to 10 carbon atoms.

The production process of the present invention will become apparent from the following description.

DETAILED DESCRIPTION OF THE INVENTION

The compound of Formula (1) of the present invention can be safely and readily converted into 2-aryl-1,3-propanediols serving as precursors for synthesizing felbamate.

In Formula (1) and in the following description, the aryl group represented by Ar may include hydrocarbon type aromatic groups and heterocyclic aromatic groups. The hydrocarbon type aromatic groups can be exemplified by a phenyl group, a naphthyl group, a tolyl group and a biphenylyl group. The heterocyclic aromatic groups can be exemplified by a furyl group and a thienyl group. These aryl groups may have a substituent. Such a substituent can be exemplified by a lower alkyl group such as a methyl group, an ethyl group, a n-propyl group, an isopropyl group, a n-butyl group, a t-butyl group, a n-pentyl group, an isoamyl group, a neopentyl group, a n-hexyl group or a cyclohexyl group, a lower alkoxy group such as a methoxy group or an ethoxy group, and a halogen atom such as chlorine or bromine.

In Formula (1) and in the following description, the $C_1$ to $C_{10}$ alkoxy group represented by $R^4$ can be exemplified by a methoxy group, an ethoxy group, a n-propoxy group, an isopropoxy group, a t-butoxy group, a cyclohexyloxy group, an octyloxy group and a decyloxy group, and these may have a substituent. Such a substituent can be exemplified by a lower alkoxy group such as a methoxy group, an ethoxy group or an isopropoxy group, an aryl group such as a phenyl group, a tolyl group or an ethylphenyl group, an aryloxy group such as a phenoxy group, an aralkoxy group such as a benzyloxy group, and a halogen atom such as chlorine or bromine.

In Formula (1) and in the following description, the $C_1$ to $C_{10}$ acyloxy group represented by $R^5$ can be exemplified by an alkanoyloxy group such as an acetoxy group, a propionyloxy group, a butanoyloxy group or an octanoyloxy group, and an aryloyloxy group such as a benzoyloxy group or a furanoyloxy group.- These acyloxy groups may have a substituent. Such a substituent can be exemplified by a lower alkyl group such as a methyl group, and a lower alkoxy group such as a methoxy group.

In Formula (1) and in the following description, the $C_1$ to $C_5$ alkyl group represented by $R^6$ or $R^7$ can be exemplified by a methyl group, an ethyl group and an isopropyl group, and these may have a substituent. Such a substituent can be exemplified by a lower alkoxy group such as a methoxy group, an aryl group such as a phenyl group, an aryloxy group such as a phenoxy group, an aralkoxy group such as a benzyloxy group, and a halogen atom such as chlorine or bromine. The $C_2$ to $C_{10}$ oligomethylene group formed by $R^6$ together with $R^7$ can be exemplified by a trimethylene group, a tetramethylene group and a pentamethylene group. These may have a substituent. Such a substituent can be exemplified by a lower alkyl group such as a methyl group, a lower alkoxy group such as a methoxy group, an aryl group such as a phenyl group, an aryloxy group such as a phenoxy group, an aralkoxy group such as a benzyloxy group, and a halogen atom such as chlorine or bromine.

As compounds of preferred embodiments, the compound of Formula (1) of the present invention can be exemplified by compounds of the following Formulas (1a), (1b), (1c) and (1d).

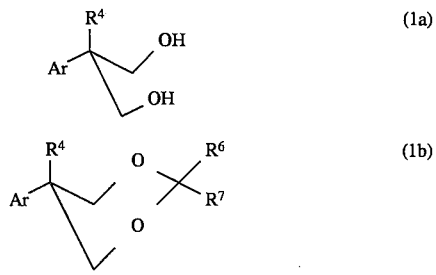

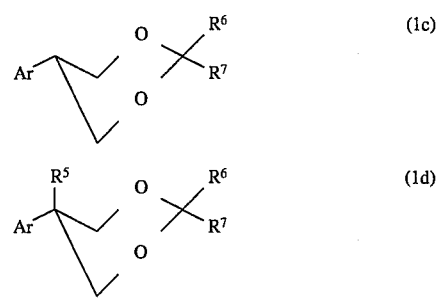

The process for producing the compound of the present invention will be described below taking an example of the whole synthesis, as shown in Scheme 1, in which an epoxide of Formula (3) is used as a starting material and a 2-aryl-1,3-propanediol of Formula (B) is obtained through the novel compounds of Formulas (1a) to (1d) according to preferred embodiments of the present invention.

In Scheme 1, Step a. is concerned with a novel process for producing a glycol monoether of Formula (4); Step b., a novel process for producing an ether-substituted aldehyde of Formula (5); and Step d., a novel process for producing the 2-aryl-1,3-propanediol of Formula (B) from the compound of Formula (1a) of the present invention.

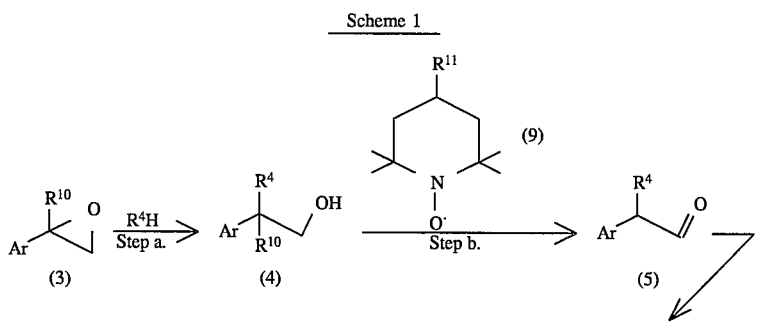

Scheme 1

-continued
Scheme 1

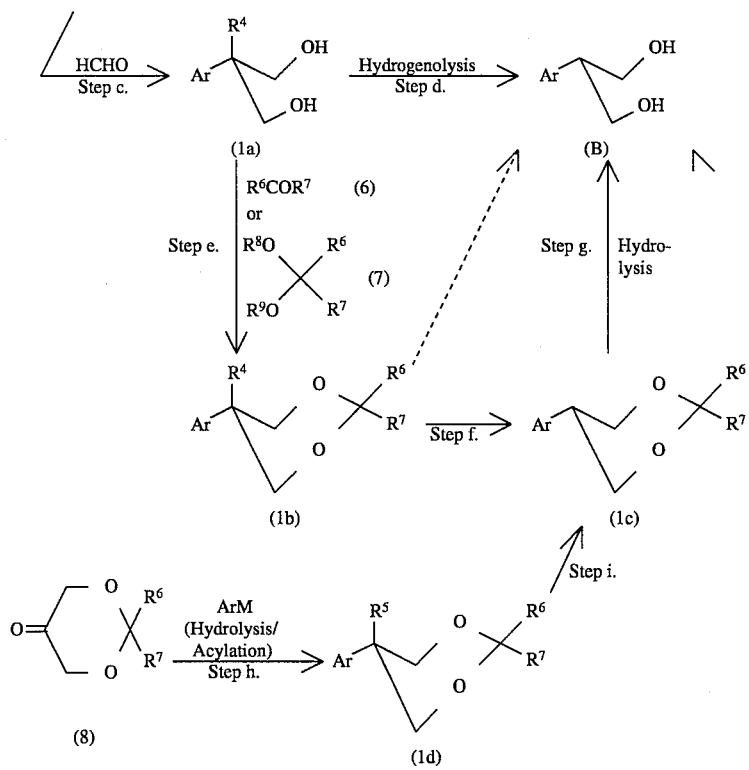

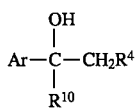

Step a.

As stated above, this step is concerned with a novel process for producing a glycol monoether represented by Formula (4) that can be utilized as a starting material for agricultural chemicals or antiepileptics. As a process for obtaining the compound represented by Formula (4), a process in which an epoxide and an alcohol are allowed to react with each other in the presence of an acid catalyst such as sulfuric acid [Japanese Patent Publication No. 5-52819; J. Am. Chem. Soc. 72, 1480 (1950)] and a process in which an epoxide and an alcohol are allowed to react with each other in the presence of a catalyst comprising a perfluorosulfonic acid type ion exchange resin (trade name: NAFION-H; available from E. I. du Pont de Nemours and Company) [Synthesis 280 (1981)] are known in the art.

In the process in which an epoxide and an alcohol are allowed to react with each other in the presence of an acid catalyst such as sulfuric acid, a compound comprising an isomer represented by Formula (4a) is formed as a by-product in a large quantity in addition to the desired compound represented by Formula (4).

$$\begin{array}{c} OH \\ | \\ Ar-C-CH_2R^4 \\ | \\ R^{10} \end{array} \quad (4a)$$

In this case, the desired compound represented by Formula (4) and the by-product compound represented by Formula (4a) are similar to each other in their physical properties such as boiling point, and hence the desired compound with a high purity can not be obtained in a high yield.

In the process for obtaining 2-phenyl-2-alkoxyethan-1-ol by allowing a styrene oxide to react with an alcohol in the presence of a catalyst comprising a perfluorosulfonic acid type ion exchange resin, the cationic ion exchange resin used as a catalyst is expensive compared with general-purpose cationic ion exchange resins having a sulfonic acid group and is not practical when the process is carried out in an industrial scale.

Accordingly, in the present step, an epoxide of Formula (3) (in Formula (3) and in the following description, $R^{10}$ represents a hydrogen atom or an alkyl group having 1 to 6 carbon atoms such as a methyl group or an ethyl group, and this alkyl group may have a substituent including a lower alkoxy group such as a methoxy group, a halogen atom such as chlorine and an aryl group such as a phenyl group) and an alcohol $R^4H$ are allowed to react with each other in the presence of a catalyst comprising a cation exchange resin having been washed with an alcohol. This makes it possible to obtain the compound of Formula (4) in a high conversion and a high yield, without substantially any formation of the by-product of Formula (4a).

The cation exchange resin preferably usable may include those in which cation exchange groups are sulfonic acid groups, and general-purpose polystyrenesulfonic acid resins made to have a three-dimensional structure by cross-linking can be used.

As the alcohol used to wash the cation exchange resin, alcohols as exemplified by methanol, ethanol, n-propanol, n-butanol, isopropanol and isoamyl alcohol can be used. The same one as the alcohols $R^4H$ directly participating in the reaction in Step a. may also be used.

With regard to the proportion of the epoxide of Formula (3) and the alcohol represented by $R^4H$, the use of the alcohol in an excessively smaller amount than the epoxide may result in a low selectivity in the formation of the glycol monoether of Formula (4), and on the other hand the use of the alcohol in an amount excessively larger than the epoxide may result in a decrease in volumetric efficiency.

Hence, the alcohol represented by $R^4H$ may preferably be used in an amount of from 1 mole to 20 moles, and more preferably from 2 moles to 10 moles, per mole of the epoxide of Formula (3).

When the epoxide of Formula (3) is allowed to react with the alcohol represented by $R^4H$, a decrease in yield of the desired glycol monoether of Formula (4) may be caused if the cation exchange resin having been washed with an alcohol, used as the catalyst, is in an excessively large amount.

Hence, the cation exchange resin having been washed with an alcohol, used as the catalyst, should be used in amount of from about 0.01 to 10.0% by weight, and preferably from about 0.05 to 3.0% by weight, based on the weight of the epoxide of Formula (3).

A lower reaction temperature at the time the epoxide of Formula (3) is allowed to react with the alcohol represented by $R^4H$ makes the rate of reaction lower, and a higher reaction temperature makes the side reaction vigorous to give the by-product formed in a larger quantity. Hence, when the process of the present invention is carried out, the reaction temperature should be controlled to from $-20°$ to $100°$ C., and preferably from $-10°$ to $50°$ C.

Step b.

This step is concerned with a novel process for producing a 2-alkoxy-2-arylethan-1-al represented by Formula (5) that can be utilized as a starting material for agricultural chemicals or antiepileptics.

As one of leading processes for obtaining the compound represented by Formula (5), a process in which the compound of Formula (4), the product in Step a., is oxidized is hitherto known in the art [R. Annunziata et al., J. Chem. Soc. Parkin Trans., 1, 255 (1985)]. This process is commonly called Swern oxidation, which can be effective for scientific experiments, but is a process not so practical. This is because an oxidizing agent used in this process is dimethyl sulfoxide, and, as a result of the reaction, dimethyl sulfide is produced, which gives out a disagreeable odor. Moreover, the reaction must be carried out at a low temperature of around $-60°$ C., and hence not only an energy cost is required for cooling but also expensive oxalyl chloride must be used as an oxidation activator. Thus, it is difficult to carry out the process in an industrial scale.

In J. Org. Chem., 52, 2559, (1987), P. L. Anelli et al. have reported that an aldehyde is obtained by oxidizing a primary alcohol using sodium hypochlorite as an oxidizing agent and N-oxyradical as a catalyst, in the presence of bromide ions as a co-catalyst and in a two-phase solvent of methylene chloride and water using sodium hydrogencarbonate as a pH adjuster. However, no example for synthesizing 2-alkoxy-2-arylethan-1-al has been reported.

Now, in the present step, when the 2-alkoxy-2-arylethan-1-ol of Formula (4) (where $R^{10}$ is hydrogen) is oxidized, a hypochlorite is used as an oxidizing agent in the presence of an N-oxyradical as a catalyst of Formula (9), i.e., 4-substituted-2,2,6,6-tetramethylpiperidine-1-oxyl. At this time, the reaction is carried out in a two-phase solvent of water and an organic solvent. This makes it possible to produce aldehydes of Formula (5) at a low cost and in an industrially advantageous manner.

The hypochlorite used as an oxidizing agent in the present step includes, for example, alkali metal hypochlorites such as sodium hypochlorite and potassium hypochlorite, and alkaline earth metal salts of hypochloric acid as typified by calcium hypochlorite. Of these, what can be particularly preferably used is an aqueous solution of sodium hypochlorite, which is inexpensive and readily available.

The hypochlorite may preferably be used in an amount not less than equimolecular amount based on the aromatic glycol monoether of Formula (4). Since, however, use of the oxidizing agent in an excessive quantity may further oxidize the aldehyde to form a by-product carboxylic acid, the reaction may preferably be carried out using the oxidizing agent in an amount of approximately from 1 to 2 equimolecular amount based on the aromatic glycol monoether of Formula (4).

In the N-oxyradical of Formula (9) used as a catalyst in the present step, $R^{11}$ represents a hydrogen atom, an alkyl group having 1 to 10 carbon atoms as exemplified by a methyl group, an ethyl group, a n-propyl group, an isopropyl group, a n-butyl group, a n-pentyl group, an isoamyl group, a neopentyl group, a n-hexyl group, an isohexyl group, a heptyl group, an octyl group, a nonyl group or a decyl group, an alkoxy group having 1 to 10 carbon atoms as exemplified by a methoxy group, an ethoxy group, a n-propoxy group, an isopropoxy group, a n-butoxy group, a n-pentyloxy group, an isoamyloxy group, a neopentyloxy group, a n-hexyloxy group, an isohexyloxy group, a heptyloxy group, an octyloxy group, a nonyloxy group or a decyloxy group, an aralkoxy group having 1 to 10 carbon atoms as exemplified by a benzyloxy group, a phenylethoxy group or a cinnamyloxy group, or an acyloxy group having 1 to 10 carbon atoms as exemplified by a formyloxy group, an acetoxy group, a propionyloxy group, a butyryloxy group, an isobutyryloxy group, a valeryloxy group, an isovaleryloxy group, a hexanoyloxy group, a heptanoyloxy group, an octanoyloxy group, a nonanoyloxy group or a decanoyloxy group.

Preferred N-oxyradical catalysts of Formula (9) are those in which $R^{11}$ is an alkoxy group, aralkoxy group or acyloxy group having 1 to 10 carbon atoms. Those having 4 to 10 carbon atoms are particularly preferred.

The N-oxyradical catalyst of Formula (9) may preferably be used in an amount as small as possible since this catalyst is expensive. In order to obtain a satisfactory effect for adding the catalyst, it may be used in an amount of from 0.001 to 5 moles, and preferably from 0.01 to 1 mole%, based on the compound of Formula (4).

With regard to the organic solvent used in the present step, there are no particular limitations thereon so long as they are not affected under reaction conditions. It may include, for example, saturated hydrocarbons, aromatic hydrocarbons and chlorine-substituted hydrocarbons. Of these, particularly preferred organic solvents are saturated chain hydrocarbons, saturated cyclic hydrocarbons or aromatic hydrocarbons having 5 to 10 carbon atoms, as specifically exemplified by hexane, heptane, cyclopentane, cyclohexane, benzene, toluene, xylene and mesitylene. Any of these organic solvents are used together with water to form a two-phase solvent.

The organic solvent usually dissolves the aromatic glycol monoether of Formula (4) and also is used in an enough amount to dissolve the N-oxyradical, i.e., in an amount of from 0.1 time to 5 times by weight, and preferably from 1 time to 3 times by weight, based on the weight of the aromatic glycol monoether. With regard to the water, the oxidizing agent hypochlorite is commonly commercially available in the form of an aqueous solution, and the water contained therein can be enough in amount. On account of operation, the water may also be kept present in advance in a reaction vessel. In view of operation and yield, the organic solvent and the water may preferably be used finally in a proportion ranging from 1:5 to 5:1 in weight ratio.

In the oxidation reaction in the present step, a metal halide such as a metal bromide or a metal iodide may preferably be used as a co-catalyst or promoter. In particular, the reaction may preferably be carried out in the presence of a metal bromide such as sodium bromide, potassium bromide or a copper bromide. Use of the metal halide brings about a more improvement in the yield of the desired compound ether-substituted aldehyde of Formula (5).

The metal bromide may usually be used in an amount ranging from 0.1 to 100 mole% based on the aromatic glycol monoether. Taking account of the efficiency of reaction and the cost of metal bromides, it may preferably be used in an amount ranging from 1 to 10 mole%.

The oxidation reaction in the present step can be affected by the pH (hydrogen ion concentration) of the aqueous phase. In such an instance, for the purpose of adjusting the pH, an alkali phosphate or an alkali carbonate may be added in the reaction system to carry out the reaction.

Any of these pH adjusters should be used in such an amount, depending on the type of the reagent used, that the pH comes to range from 8 to 10 in the course of the reaction. For example, in the case of sodium hydrogencarbonate, its use in an amount of from 5 to 30 mole% based on the starting aromatic glycol monoether can keep the pH within that range.

When the oxidation reaction of the present step is carried out, the reaction may be carried out at a temperature so selected as to range from $-20°$ C. to $100°$ C., and preferably from $0°$ C. to $60°$ C.

After the reaction has been completed, the reaction mixture is separated into an organic layer and an aqueous layer, the organic layer is separated out, and the solvent is evaporated, followed by operation of distillation purification or the like, so that the desired compound ether-substituted aldehyde can be isolated.

As the starting compound of Formula (4) in the present step, it is preferable to use the one produced in Step a. Without limitation thereto, it is also possible to use those produced by other processes. For example, the compound of Formula (4) can also be synthesized by reacting an epoxide and an alcohol in the presence of an acid catalyst such as sulfuric acid [Japanese Patent Publication No. 5-52819; J. Am. Chem. Soc. 72, 1480 (1950)] or by allowing an epoxide to react with an alcohol in the presence of a catalyst comprising a perfluorosulfonic acid type ion exchange resin (trade name: NAFION-H; available from E. I. du Pont de Nemours and Company) [Synthesis 280 (1981)] are known in the art.

Step c.

This step is the step of producing the compound of Formula (1a), which is an embodiment of the compound of the present invention, from the compound of Formula (5). This step is included in the category called the Tollens reaction. Stated specifically, the compound of Formula (1a) can be obtained by allowing the compound of Formula (5) to react with formalin under basic conditions, e.g., in the presence of a basic catalyst.

In the present step, the reaction can be carried out without addition of any particular solvent. It is preferable to use hydrophilic solvents as exemplified by lower alcohols such as methanol, ethanol and propanol, water-soluble ethers such as tetrahydrofuran, dioxane and dimethoxyethane, as well as dimethyl sulfoxide, sulfolane and N,N-dimethylformamide.

With regard to the formalin used as a reaction reagent, it is economical to use an aqueous 10–50% formalin solution, which is readily available. Any formaldehyde sources such as pure formaldehyde, paraformaldehyde and trioxane may also be used.

The formalin used as a reaction reagent may be in an amount of 2 equimolecular amount or more without any limitations up to a large excess, based on the 2-alkoxy-2-phenylethan-1-al of Formula (5). From the viewpoint of reaction rate and economical advantages, it may preferably be used in an amount of from 2 to 4 equimolecular amount.

The basic catalyst in the presence of which the 2-alkoxy-2-phenylethan-1-al of Formula (5) is allowed to react with formalin may include hydroxides, carbonates, hydrogencarbonates or acetates of alkali metals or alkaline earths, as exemplified by sodium hydroxide, potassium hydroxide, calcium hydroxide, magnesium hydroxide, barium hydroxide, sodium carbonate and potassium carbonate.

The basic catalyst may be used in an amount of 1 equimolecular amount based on the 2-alkoxy-2-phenylethan-1-al of Formula (5) from the viewpoint of a mechanism of this reaction. In order to complete the reaction, it may preferably be used in an amount of from 1.1 to 3.0 equimolecular amount.

The reaction temperature at which the 2-alkoxy-2-phenylethan- 1-al of Formula (5) is reacted with formalin may be from $-10°$ to $200°$ C., and preferably from $10°$ to $100°$ C.

Step d.

This step is the step of producing a 2-aryl-1,3-propanediol of Formula (B) by subjecting the compound of Formula (1a) obtained in Step c., to hydrogenolysis in a solvent in the presence of a catalyst. The 2-aryl-1,3-propanediol of Formula (B) can be safely and simply produced through this step.

In this step, the yield of the compound of Formula (B) based on the compound of Formula (1a) is about 40%.

With regard to the solvent used when the 2-alkoxy-2-phenyl- 1,3-propanediol of Formula (1a) or a derivative thereof is subjected to hydrogenolysis, there are no particular limitations thereon so long as it does not inhibit the reaction and can dissolve the 2-alkoxy-2-phenyl-1,3-propanediol of Formula (1a) or a derivative thereof. For example, it is possible to use lower alcohols such as methanol, ethanol, n-propanol, isopropanol, n-butanol, sec-butanol and isoamylalcohol, ethers such as diethyl ether, diisopropyl ether, tetrahydrofuran and dimethoxyethane, saturated hydrocarbons such as n-hexane and n-heptane, aromatic hydrocarbons such as benzene, toluene, xylene and mesitylene, aliphatic carboxylic acids such as formic acid and acetic acid, esters such as methyl acetate and ethyl acetate, amides such as N,N-dimethylformamide and N-methylpyrrolidone, sulfur-containing solvents such as dimethyl sulfoxide and sulfolane, and also mixed solvents of two or more kinds of these.

The catalyst used when the 2-alkoxy-2-phenyl-1,3-propanediol of Formula (1a) or a derivative thereof is subjected to hydrogenolysis may include catalysts commonly used for hydrogenation. For example, Ranney nickel, nickel on diatomaceous earth, palladium black, activated carbon- or alumina-supported palladium, platinum black, and activated carbon- or alumina-supported platinum are preferred.

As hydrogen sources used when the 2-alkoxy-2-phenyl-1,3-propanediol of Formula (1a) or a derivative thereof is subjected to hydrogenolysis, any of molecular hydrogen, formic acid, sodium formate, ammonium formate, triethylammonium formate, sodium dihydrogenphosphite, hydrazine, cyclohexene and dicyclohexene can be used.

The hydrogenolysis may be carried out at a pressure of from normal pressure to $300$ kg/cm$^2$, and preferably from $0$ to $100$ kg/cm$^2$, and at a temperature of from $-20°$ to $300°$ C., and preferably from $0°$ to $200°$ C.

Through the foregoing step, the 2-alkoxy-2-phenyl-1,3-propanediol of Formula (1a) or a derivative thereof is hydrogenolyzed, thereafter the catalyst is removed from the reaction mixture by filtration or the like, optionally followed by washing with water and solvent extraction and further followed by purification such as distillation or recrystallization, so that the 2-phenyl-1,3-propanediol of Formula (B) or a derivative thereof can be obtained.

Steps e., f. and g.

Step e. and the next Step f. are steps of converting the compound of Formula (1a) into the compound of Formula (1c) via the compound of Formula (1b) so that the 2-aryl-1,3-propanediol of Formula (B) can be obtained in a higher yield than in Step d. The compound of Formula (1c) can give the compound of Formula (B) with greater ease and in a higher yield by hydrolysis as will be detailed in Step g. described later. The respective steps will be described below.

Step e.

In this step, the compound of Formula (1a) is allowed to react with the compound of Formula (6) or (7) in the presence of an acid catalyst to acetalate or ketalate the two hydroxy groups of the compound of Formula (1a), and is thereby brought to the compound of Formula (1b).

The compound of Formula (6) can be specifically exemplified by aldehydes such as formaldehyde, acetaldehyde, propionaldehyde, butylaldehyde, isobutylaldehyde, valeraldehyde and isovaleraldehyde, acetone, and ketones such as methyl ethyl ketone, diethyl ketone, methyl isopropyl ketone, cyclopentanone and cyclohexanone.

In Formula (7) and in the following description, $R^8$ and $R^9$ each independently represent an alkyl group having 1 to 10 carbon atoms, or $R^8$ and $R^9$ together form an oligomethylene group having 2 to 10 carbon atoms. The $C_1$ to $C_{10}$ alkyl group represented by $R^8$ or $R^9$ can be exemplified by a methyl group, an ethyl group, an isopropyl group, a hexyl group and an octyl group. These groups may have a substituent. Such a substituent can be exemplified by a lower alkoxy group such as a methoxy group, an aryl group such as a phenyl group, an aryloxy group such as a phenoxy group, an aralkoxy group such as a benzyloxy group, and a halogen atom such as chlorine or bromine. The $C_2$ to $C_{10}$ oligomethylene group formed by $R^8$ together with $R^9$ can be exemplified by a trimethylene group, a tetramethylene group and a pentamethylene group. These groups may have a substituent. Such a substituent can be exemplified by a lower alkyl group such as a methyl group, a lower alkoxy group such as a methoxy group, an aryl group such as a phenyl group, an aryloxy group such as a phenoxy group, an aralkoxy group such as a benzyloxy group, and a halogen atom such as chlorine or bromine. The compound of Formula (7) can be exemplified by acetaldehyde dimethylacetal, acetone dimethyl acetal, acetone diethyl acetal, 2,2-dimethyl-1,3-dioxolane and cyclohexanone dimethyl acetal.

The acid catalyst used in the present step may include mineral acids such as sulfuric acid, hydrochloric acid and phosphoric acid, organic sulfonic acids such as benzenesulfonic acid, p-toluenesulfonic acid, methanesulfonic acid and trifluoromethanesulfonic acid, carboxylic acids such as trifluoroacetic acid, and acid salts formed from these mineral acids, organic sulfonic acids or carboxylic acids, as well as acidic ion exchange resins, any of which may be used.

The reaction for acting the 2-alkoxy-2-aryl-1,3-propanediol of Formula (1a) or a derivative thereof and the carbonyl compound of Formula (6) upon each other in the presence of the acid catalyst can be made to proceed by removing water formed.

The water thus formed can be removed by distillation, or azeotropic distillation with addition of a solvent capable of forming an azeotrope with water, such as hexane, heptane or toluene, or using a method in which an inorganic dehydrating agent such as magnesium sulfate or molecular sieve, or an organic dehydrating agent comprised of an orthocarboxylate such as orthformate or orthoacetate or an acetal such as acetone dimethyl acetal, is made present in the system in an equimolar or more amount based on the water formed.

The reaction for acting the 2-alkoxy-2-aryl-1,3-propanediol of Formula (1a) or a derivative thereof and the acetal of Formula (7) upon each other in the presence of the acid catalyst can be made to proceed by removing alcohols represented by $R^8OH$ and $R^9OH$ formed.

The alcohols thus formed can be removed by distillation, or azeotropic distillation with addition of a solvent capable of forming an azeotrope with the alcohols.

In the reaction of the carbonyl compound of Formula (6) or the acetal of Formula (7), the carbonyl compound of Formula (6) or the acetal of Formula (7) should be approximately in an amount of from 1 mole to 5 moles, and preferably from 1 mole to 2 moles, per mole of the 2-alkoxy-2-aryl-1,3-propanediol of Formula (1a) or a derivative thereof. Also, this reaction may be carried out at a temperature of from −20° to 250° C., and preferably from 0° to 150° C.

When the compound of Formula (1b) obtained in the present step is converted into the compound of Formula (B), it can be converted into the compound of Formula (B), without especially isolating the compound of Formula (1c), by hydrogenolysis carried out in the presence of a palladium catalyst according to a conventional method and further followed by hydrolysis. In order to improve the yield and obtain products with a high purity, the compound of Formula (1c) may preferably be isolated first.

Step f.

This step is the step of subjecting the compound of Formula (1b) to hydrogenolysis in a solvent in the presence of a palladium catalyst to obtain the compound of Formula (1c).

The palladium catalyst used in the present step may include palladium catalysts used in usual hydrogenolysis, as exemplified by activated carbon-supported palladium, alumina-supported palladium, calcium carbonate-supported palladium, palladium black and activated carbon-supported palladium hydroxide. In particular, activated carbon-supported palladium is preferred.

As the solvent used when the hydrogenolysis is carried out, it is possible to use saturated lower alcohols such as methanol, ethanol, n-propanol, isopropanol, n-butanol, sec-butanol, tert-butanol and isoamyl alcohol, carboxylates such as methyl acetate and ethyl acetate, ethers such as diisopropyl ether, tetrahydrofuran and 1,4-dioxane, aromatic hydrocarbons such as benzene, toluene and xylene, lower carboxylic acids such as formic acid and acetic acid, as well as N,N-dimethylformamide and dimethyl sulfoxide. In particular, lower alcohols are preferred.

As hydrogen sources used when the hydrogenolysis is carried out, molecular hydrogen is preferred. Formic acid and formic acid ammonium salts such as ammonium formate and triethylammonium formate, and olefins such as cyclohexene and 1,4-cyclohexadiene serving as hydrogen donors may also be used. When molecular hydrogen is used as a hydrogen source, a reacton accelerator including acids such as formic acid, acetic acid, trifluoroacetic acid, methanesulfonic acid, trifluoromethanesulfonic acid, benzenesulfonic acid, p-toluenesulfonic acid, dodecylbenzenesulfonic acid and hydrochloric acid may be added in a small amount.

The acid added as a reaction accelerator may be in an amount, variable depending on the type of the acid, of not more than 20 moles, and preferably not more than 10 mole%, based on the compound of Formula (1b) or a derivative thereof used.

The hydrogenolysis reaction in the present step can be carried out at 0° to 200° C. Since the reaction may proceed slowly at low temperatures and the selectivity may decrease at high temperatures, the hydrogenolysis may preferably be carried out at 20° to 150° C.

Step g.

This step is the step of subjecting the compound of Formula (1c) to hydrolysis to obtain the 2-aryl-1,3-propanediol of Formula (B). The hydrolysis reaction in this step can be carried out by a conventional method. For example, it can be carried out by adding the compound of Formula (1c) in 1N-hydrochloric acid followed by stirring at 30° C. The compound of Formula (B) can be separated from the reaction mixture also by a conventional method.

When the compound of Formula (B) is produced successively through the steps of e., f. and g. in this way, its yield from the compound of Formula (1a) can be improved from the yield of about 40% in Step d. up to an yield of about 80%.

Steps h. and i.

These steps are concerned with a process for producing the compound of Formula (1) in which $R^1$ is $R^5$, i.e., the compound of Formula (1d), and a process for producing the compound of Formula (1c) from the resulting compound of Formula (1d). The respective steps will be described below.

Step h.

In this step, a 1,3-dioxan-5-one derivative of Formula (8) is allowed to react with an aryl metal reagent having an aryl group (Ar). As the aryl metal reagent, any of reagents that can add an aryl group to a carbonyl group as an anion can be used, as exemplified by Grignard reagents such as aryl magnesium halides, and aryl lithium, aryl copper, diaryl cuprates or highly coordinated copper compounds.

As the aryl magnesium halides, any of aryl magnesium chlorides, aryl magnesium bromides and aryl magnesium iodides may be used.

When a Grignard reagent or aryl lithium is used as the aryl metal reagent, a catalyst such as a monovalent copper reagent or a cerium reagent, e.g., cerium chloride may also be used.

The aryl metal reagent may be used in an amount of from about 1.01 to 5.0 equimolecular amount based on the 1,3-dioxan-5-one of Formula (8) or a derivative thereof; from the viewpoint of economical advantages and operability, preferably in an amount of from about 1.05 to 1.5 equimolecular amount.

As solvents used in the present step, it is possible to use aliphatic hydrocarbons such as hexane and heptane, aromatic hydrocarbons such as benzene and toluene, and ethers such as diethyl ether, tetrahydrofuran, diisopropyl ether and 1,4-dioxane.

The reaction in the present step can be carried out in a wide temperature range of from −70° to 200° C. From the viewpoint of operability and so forth, it may preferably be carried out at −20° to 100° C.

The compound in which $R^5$ is OH can be obtained, after the reaction of the 1,3-dioxan-5-one of Formula (8) or a derivative thereof with the aryl metal reagent has been completed, by treatment with an aqueous weakly acidic solution as exemplified by an aqueous ammonium chloride solution, followed by operation for its isolation as it is.

The compound in which $R^5$ is an acyloxy group having 1 to 10 carbon atoms can be obtained, after the reaction of the 1,3-dioxan-5-one of Formula (8) or a derivative thereof with the aryl metal reagent has been completed, by treatment with an aqueous weakly acidic solution as exemplified by an aqueous ammonium chloride solution, followed by operation for its isolation, and thereafter the product thus isolated is reacted with a corresponding acylating agent. Alternatively, immediately after the reaction of the 1,3-dioxan-5-one of Formula (8) or a derivative thereof with the aryl metal reagent has been completed, a corresponding acylating agent is reacted, followed by addition of water to carry out isolation.

The acylating agent may include acid chlorides such as acetyl chloride and benzoyl chloride, and acid anhydrides such as acetic anhydride and benzoic anhydride, any of which can be used. The acylating agent may be used in an amount of from about 1.01 to 5.0 equimolecular amount based on the reaction product of the 1,3-dioxan-5-one of Formula (8) or a derivative thereof with the aryl metal reagent; from the viewpoint of economical advantages and operability, preferably in an amount of from about 1.05 to 1.2 equimolecular amount.

The compound obtained through the foregoing operation can be readily purified by distillation.

When the compound of Formula (1d) obtained in the present step is converted into the compound of Formula (B), it can be converted into the compound of Formula (B), without especially isolating the compound of Formula (1c), by hydrogenolysis carried out in the presence of a palladium catalyst according to a conventional method and further followed by hydrolysis. In order to improve the yield and obtain products with a high purity, the compound of Formula (1c) may preferably be isolated first.

Step i.

This step is the step of hydrogenolyzing the compound of Formula (1d) into the compound of Formula (1c), which can be carried out under the same conditions as the Step f. previously described. The resulting compound of Formula (1c) can also be converted into the compound of Formula (B) under the same conditions as the Step g. previously described.

EXAMPLES

The present invention will be specifically described below by giving Examples.

The respective steps in Scheme 1 and Examples correspond as shown below, provided that Example 19 is an example in which the compound of Formula (B) is produced from the compound of Formula (1b) and Example 27 is an example in which the compound of Formula (B) is produced from the compound of Formula (1d).

| Steps | Examples |
| --- | --- |
| a. | 1 to 2 |
| b. | 3 to 5 |
| c. | 6 to 10 |
| d. | 11 to 15 |
| e. | 16 to 18 |
| f. | 20 to 22 |
| g. | 23 |
| h. | 24 to 26 |

EXAMPLE 1

Polystyrenesulfonic acid made to have a three-dimensional structure by cross-linking was washed with methanol and then dried to obtain a cation exchange resin used as a catalyst in the present Example. Thereafter, 5 g of this cation exchange resin and 3 kg of methanol were charged into a reaction vessel, and the temperature inside the reaction vessel was adjusted to 10° C.

Next, 1 kg of styrene oxide was fed into the reaction vessel over a period of 5 hours. Throughout the feeding of styrene oxide and also after the feeding, the temperature of the reaction solution was kept at about 20° C. Then, in that state, the reaction solution was stirred for 6 hours, where the reaction was completed.

Subsequently, the catalyst and methanol were removed from the reaction product solution, followed by distillation under reduced pressure to obtain 1,207 g of the desired compound 2-methoxy-2-phenylethan-1-ol (yield: 95.3%; purity: 99%).

EXAMPLE 2

Polystyrenesulfonic acid made to have a three-dimensional structure by cross-linking was washed with propanol and then dried to obtain a cation exchange resin used as a catalyst in the present Example. Thereafter, 5 g of this cation exchange resin and 3 kg of propanol were charged into a reaction vessel, and the temperature inside the reaction vessel was adjusted to 10° C.

Next, 1 kg of styrene oxide was fed into the reaction vessel over a period of 5 hours. Throughout the feeding of styrene oxide and also after the feeding, the temperature of the reaction solution was kept at about 25° C. Then, in that state, the reaction solution was stirred for 12 hours, where the reaction was completed.

Subsequently, the catalyst and propanol were removed from the reaction mixture, followed by distillation under reduced pressure to obtain 1,437 g of the desired compound 2-propoxy-2-phenylethan-1-ol (yield: 95.8%; purity:

Comparative Example 1

Into a reaction vessel, 0.5 g of a cation exchange resin comprising polystyrenesulfonic acid having a three-dimensional structure but not washed with an alcohol and 300 g of propanol were charged, and the temperature inside the reaction vessel was adjusted to 10° C.

Next, 100 g of styrene oxide was fed into the reaction vessel over a period of 5 hours. Throughout the feeding of styrene oxide and also after the feeding, the temperature of the reaction solution was kept at about 25° C. Then, in that state, the reaction solution was stirred for 12 hours, where the reaction was completed.

Subsequently, the catalyst and propanol were removed from the reaction mixture, followed by distillation under reduced pressure to obtain 187.75 g of the desired compound 2-propoxy-2-phenylethan-1-ol (yield: purity: 94%). The yield in this Comparative Example was lower than that in Examples 1 and 2.

EXAMPLE 3

Into a reaction vessel, 180.25 g of 2-phenyl-2-propoxyethanol, 1.31 g of 4-benzyloxy-2,2,6,6-tetramethylpiperidine- 1-oxyl, 5.15 g of sodium bromide, 30.64 g of sodium bicarbonate, 200 g of water and 540 g of toluene were charged, and the temperature inside the reaction vessel was adjusted to 20° C. While the mixture in the reaction vessel was vigorously stirred, an aqueous 13% sodium hypochlorite solution was dropwise added thereto over a period of 30 minutes. After the addition was completed, the stirring was continued in that state for 10 minutes, where the reaction was completed.

After the lower layer was removed by separation, the organic layer was washed with water. After the toluene was removed from the organic layer, the residue was distilled under reduced pressure to obtain 135.4 g of 2-phenyl-2-propoxyethanal (yield: 76%).

EXAMPLE 4

The procedure in Example 3 was repeated except that 180.25 g of 2-phenyl-2-propoxyethanol was replaced with 152 g of 2-methoxy-2-phenylethanol, to obtain 104.8 g of 2-phenyl-2-methoxyethanal (yield: 69%).

EXAMPLE 5

The procedure in Example 3 was repeated except that 180.25 g of 2-phenyl-2-propoxyethanol was replaced with 194 g of 2-butoxy-2-phenylethanol and 540 g of toluene was replaced with 580 g of cyclohexane, to obtain 130.5 g of 2-butoxy- 2-phenylethanal (yield: 68%).

EXAMPLE 6

In 15 ml of methanol, 6.17 g (30.1 mmole) of 2-ethoxy-2-phenylethanal with a purity of 80% was dissolved, and thereafter 6.0 g (60.2 mmole) of an aqueous formaldehyde solution was added thereto.

Subsequently, 5.4 g of potassium carbonate was quickly added, whereupon exothermic reaction took place, and the temperature of the reaction solution rose to 35° C. This reaction mixture was kept at 60° C. for 2 hours, where the reaction was completed.

Thin-layer chromatography (TLC) was carried out to make sure that the 2-ethoxy-2-phenylethanal had disappeared from the reaction mixture. Thereafter, the reaction solution was cooled to room temperature and was further diluted with isopropyl ether.

Next, after washing successively with 2N-hydrochloric acid water, saturated sodium bicarbonate water and brine, the organic layer was dried with anhydrous magnesium sulfate, followed by concentration under reduced pressure to obtain 7.24 g of a brown oily syrup.

This brown oily syrup was purified by column chromatography (silica gel; hexane/ethyl acetate: 3/1 to 1/1) to obtain 6.19 g of yellow oil.

The yellow oil thus obtained was dissolved in 50 ml of a hexane/ethyl acetate (4/1) mixed solvent and thereafter cooled to −20° C. to obtain 3.46 g of 2-ethoxy-2-phenyl-1,3-propanediol in the form of white crystals.

The yield of 2-ethoxy-2-phenyl-1,3-propanediol was 59.8%.

EXAMPLE 7

The procedure in Example 6 was repeated except that 2-ethoxy-2-phenylethanal was replaced with 2-methoxy-2-phenylethanal, to obtain 2-methoxy-2-phenyl-1,3-propanediol.

EXAMPLE 8

The procedure in Example 6 was repeated except that 2-ethoxy-2-phenylethanal was replaced with 2-propoxy-2-phenylethanal, to obtain 2-propoxy-2-phenyl-1,3-propanediol.

EXAMPLE 9

The procedure in Example 6 was repeated except that 2-ethoxy-2-phenylethanal was replaced with 2-isopropoxy-2-phenylethanal, to obtain 2-isopropoxy-2-phenyl-1,3-propanediol.

EXAMPLE 10

The procedure in Example 6 was repeated except that 2-ethoxy-2-phenylethanal was replaced with 2-benzyloxy-2-phenylethanal, to obtain 2-benzyloxy-2-phenyl-1,3-propanediol.

Melting points of the 2-alkoxy-2-phenyl-1,3-propanediols thus obtained in Examples 6 to 10 are shown in Table 1.

TABLE 1

| Compound of: | Melting point (°C.) |
| --- | --- |
| Example 6 | 91.1–91.9 |
| Example 7 | 97.7–98.7 |
| Example 8 | 71.6–72.5 |
| Example 9 | 52.9–53.9 |
| Example 10 | 83.4–84.3 |

Results of $^1$H-NMR analyses (solvent: $CDCl_3$; chemical shift, δ) of the 2-alkoxy-2-phenyl-1,3-propanediols obtained in Examples 6 to 10 are shown in Table 2.

TABLE 2

| Compound of: | Results of $^1$H-NMR analysis ($CDCl_3$, δ) |
| --- | --- |
| Example 6 | 1.24(t, J=6.6Hz, 3H), 2.57(d, J=6.0Hz, 1H), 2.59(d, J=7.0Hz, 1H), 3.44(q, J=6.6Hz, 2H), 3.98(dd, J=12.0, 6.0Hz, 2H), 4.07 (dd, J=12.0, 7.0Hz, 2H), 7.25–7.45(m, 5H) |
| Example 7 | 2.97(d, J=6.0Hz, 1H), 2.99(d, J=7.0Hz, 1H), 3.25(s, 3H), 3.95(dd, J=12.0, 6.0Hz, 2H), 4.07(dd, J=12.0, 7.0Hz, 2H), 7.25–7.45 (m, 5H) |
| Example 8 | 0.94(t, J=7.5Hz, 3H), 1.55–1.75(m, 2H), 2.67(d, J=6.0Hz, 1H), 2.69(d, J=6.3Hz, 1H), 3.31(t, J=6.8Hz, 2H), 3.98(dd, J=6.0, 11.4Hz, 2H), 4.06(dd, J=6.3, 11.4Hz, 2H), 7.25–7.40(m, 5H) |
| Example 9 | 1.13(d, J=5.1Hz, 6H), 2.54(brt, J=5.7Hz, 2H), 3.68(hept, J=5.1Hz, 1H), 4.04(d, J=5.7Hz, 4H), 7.25–7.50(m, 5H) |
| Example 10 | 2.66(d, J=6.0Hz, 1H), 2.69(d, J=7.0Hz, 1H), 4.08(dd, J=12.0, 6.0Hz, 2H), 4.15(dd, J=12.0, 7.0Hz, 2H), 4.45(s, 2H), 7.30–7.50 (m, 10H) |

EXAMPLE 11

Into a 100 ml autoclave, 5 g (0.033 mole) of the 2-methoxy-2-phenyl-1,3-propanediol obtained in Example 7 and 50 ml of ethanol were charged, and 10 g of a 5% Pd/C catalyst was further added thereto, where the temperature was raised to 50° C. and the hydrogen pressure was set at 5 kg/cm$^2$.

In this state, the reaction was carried out for 6 hours. Thereafter the catalyst was removed and the ethanol was further evaporated to obtain 5.17 g of a crude product.

The crude product thus obtained was dissolved in 15 g of toluene, and then cooled to precipitate crystals.

Next, the crystals were collected by filtration, followed by drying to obtain 1.68 g (0.014 mole) of the desired product 2-phenyl-1,3-propanediol.

The yield of 2-phenyl-1,3-propanediol from 2-methoxy-2-phenyl-1,3-propanediol was 42%.

EXAMPLES 12 to 15

The respective 2-alkoxy-2-phenyl-1,3-propanediols obtained in Examples 6 and 8 to 10 were each subjected to hydrogenolysis using a 5% Pd/C catalyst, in the same procedure as described in Example 11, to obtain the desired compound 2-phenyl-1,3-propanediol.

Conditions for the hydrogenolysis and the yield of each 2-phenyl-1,3-propanediol from 2-alkoxy-2-phenyl-1,3-propanediols are shown in Table 3.

TABLE 3

| Example | Starting material | Reaction temp. (°C.) | Hydrogen pressure (kg/cm$^2$) | Reaction time (hrs) | Yield (%) |
| --- | --- | --- | --- | --- | --- |
| 12 | Example 6 | 100 | 60 | 24 | 38 |
| 13 | Example 8 | 80 | 10 | 24 | 45 |
| 14 | Example 9 | 150 | 15 | 10 | 43 |
| 15 | Example 10 | 50 | Normal | 48 | 33 |

EXAMPLE 16

To 18.2 g of 2-methoxy-2-phenyl-1,3-propanediol, 7.0 g of acetone was added, and 50 g of methylene chloride was further added thereto to dissolve them. Thereafter, 0.05 g of p-toluenesulfonic acid and 10.0 g of magnesium sulfate were added, and the mixture was stirred at 20° C. for 8 hours to carry out reaction.

Next, the magnesium sulfate was removed and the solvent was evaporated to obtain a residue. Thereafter, the residue was distilled to obtain 18.2 g of the desired compound 2,2-dimethyl-5-methoxy-5-phenyl-1,3-dioxane (yield: 82%).

EXAMPLE 17

To 18.2 g of 2-methoxy-2-phenyl-1,3-propanediol, 10.5 g of cyclohexanone was added, and 70 g of toluene was further added thereto to dissolve them. Thereafter, 0.05 g of p-toluenesulfonic acid was added, and the reaction mixture was heated to 120° C. Water formed was removed by azeotropic distillation. At the time the formation of water was completed, the reaction mixture was cooled, followed by addition of triethylamine in the system to neutralize it.

Next, the solvent was evaporated under reduced pressure to obtain a residue. Thereafter, the residue was distilled to obtain 20.4 g of the desired compound 2,2-spirocyclohexyl-5-methoxy-5-phenyl-1,3-dioxane (yield: 78%).

EXAMPLE 18

To 21.0 g of 2-propoxy-2-phenyl-1,3-propanediol, 17.3 g of cyclohexanone dimethyl acetal and 0.05 g of p-toluenesulfonic acid were added, and 100 g of toluene was further added thereto to dissolve them. Thereafter, the reaction mixture was heated to 100° C., and methanol formed was removed by distillation. At the time the formation of methanol was completed, the reaction mixture was cooled, followed by addition of triethylamine in the system to neutralize it.

Next, the solvent was evaporated under reduced pressure to obtain a residue. Thereafter, low-boiling components were evaporated from the residue under reduced pressure and the resulting residue was distilled to obtain 19.6 g of the desired compound 2,2-spirocyclohexyl-5-propoxy- 5-phenyl-1,3-dioxane (yield: 75%).

Boiling points (°C./2 Torr) of the 5-alkoxy-5-phenyl-1,3-dioxane derivatives obtained in Examples 16 to 18 set out above are shown in Table 4.

TABLE 4

| Compound of: | Boiling point (°C./2 Torr) |
|---|---|
| Example 16 | 167 |
| Example 17 | 178 |
| Example 18 | 186 |

Results of $^1$H-NMR analyses (solvent: CDCl$_3$; chemical shift, δ) of the 5-alkoxy-5-phenyl-1,3-dioxane derivatives obtained in Examples 16 to 18 are shown in Table 5.

TABLE 5

| Compound of: | Results of $^1$H-NMR analysis (CDCl$_3$, δ) |
|---|---|
| Example 16 | 1.47(S, 3H), 1.52(S, 3H), 3.16(S, 3H), 4.04(d, 2H, J=12.0Hz), 4.12(d, 2H, J=12.0Hz), 7.31–7.46(m, 5H) |
| Example 17 | 1.43–1.62(m, 6H), 1.73–1.86(m, 4H), 3.16 (S, 3H), 4.02(d, 2H, J=12.0Hz), 4.12(d, 2H, J=12.0Hz), 7.26–7.45(m, 5H) |
| Example 18 | 0.89(t, 3H, J=7.4Hz), 1.43–1.62(m, 8H), 1.73–1.86(m, 4H), 3.19(t, 3H, J=6.9Hz), 4.02(d, 2H, J=11.8Hz), 4.12(d, 2H, J=10.7Hz), 7.22–7.50(m, 5H) |

EXAMPLE 19

In 300 g of isopropyl alcohol, 40 g of the 2,2-spirocyclohexyl- 5-propoxy-5-phenyl-1,3-dioxane obtained in Example 18 was dissolved, and 0.4 g of p-toluenesulfonic acid and 2.0 g of a 10% Pd/C catalyst were further added. Reaction was carried out at a hydrogen pressure of 5 kg/cm$^2$ at 80° C. for 12 hours.

After the reaction was completed, the Pd/C catalyst was removed and the isopropyl alcohol was further evaporated, followed by addition of 100 g of toluene and 100 g of 10% hydrochloric acid to carry out hydrolysis.

Thereafter, cyclohexanone was removed, further followed by crystallization from toluene to obtain 15.2 g of 2-phenyl-1,3-propanediol (yield: 77%).

EXAMPLE 20

In 100 g of isopropyl alcohol, 30 g of 2,2-spirocyclohexyl- 5-propoxy-5-phenyl-1,3-dioxane was dissolved, and 3 g of a 10% Pd/C catalyst and 0.6 g of p-toluenesulfonic acid were further added, where the hydrogen pressure was set at 5 kg/cm$^2$ and the temperature was raised to 130° C.

At the time the desired amount of hydrogen was absorbed, the reaction was stopped, the pressure was returned to normal, and the inside of the system was neutralized. After the solvent was removed, the reaction product was purified by distillation under reduced pressure to obtain 17.80 g of the desired compound 2,2-spirocyclohexyl- 5-phenyl-1,3-dioxane (yield: 81%).

EXAMPLE 21

In 100 g of ethanol, 30 g of 2,2-spirocyclohexyl-5-methoxy- 5-phenyl-1,3-dioxane was dissolved, and 3 g of a 10% Pd/C catalyst and 0.2 g of p-toluenesulfonic acid were further added, where the hydrogen pressure was set at 5 kg/cm$^2$ and the temperature was raised to 120° C.

At the time the desired amount of hydrogen was absorbed, the reaction was stopped, the pressure was returned to normal, and the inside of the system was neutralized. After the solvent was removed, the reaction product was purified by distillation under reduced pressure to obtain 20.76 g of the desired compound 2,2-spirocyclohexyl- 5-phenyl-1,3-dioxane (yield: 78%).

EXAMPLE 22

In 300 g of isopropyl alcohol, 20 g of 2,2-dimethyl-5-methoxy-5-phenyl-1,3-dioxane was dissolved, and 2 g of a 10% Pd/C catalyst and 0.3 g of methanesulfonic acid were further added, where the hydrogen pressure was set at 5 kg/cm$^2$ and the temperature was raised to 130° C.

At the time the desired amount of hydrogen was absorbed, the reaction was stopped, the pressure was returned to normal, and the inside of the system was neutralized. After the solvent was removed, the reaction product was purified by distillation under reduced pressure to obtain 12.31 g of the desired compound 2,2-dimethyl- 5-phenyl-1,3-dioxane (yield: 71%).

Boiling points (°C./1.5 Torr) of the 5-phenyl-1,3-dioxane derivatives obtained in Examples 20 to 22 set out above are shown in Table 6.

TABLE 6

| Compound of: | Boiling point (°C./1.5 Torr) |
|---|---|
| Example 20 | 152 |
| Example 21 | 152 |
| Example 22 | 143 |

Results of $^1$H-NMR analyses (solvent: CDCl$_3$; chemical shift, δ) of the 5-phenyl-1,3-dioxane derivatives obtained in Examples 20 to 22 are shown in Table 7.

TABLE 7

| Compound of: | Results of $^1$H-NMR analysis (CDCl$_3$, δ) |
|---|---|
| Example 20 | 7.30(s, 5H), 4.0(d, 4H, J=7.5Hz), 2.0(t, 1H, J=7.5Hz), 1.40–1.80(m, 10H) |
| Example 21 | 7.30(s, 5H), 4.0(d, 4H, J=7.5Hz), 2.0(t, 1H, J=7.5Hz), 1.40–1.80(m, 10H) |
| Example 22 | 7.30(s, 5H), 3.90(d, 4H, J=7.4Hz), 1.92 (t, 1H, J=7.4Hz), 1.30(s, 3H), 1.27(s, 3H) |

EXAMPLE 23

To 100 g of 1N hydrochloric acid, 50 g of the 2,2-spirocyclohexyl- 5-phenyl-1,3-dioxane obtained in Example 20 was added, and the mixture was stirred at 30° C. for 12 hours.

Gas chromatography was carried out to make sure that the reaction was completed, cyclohexanone formed was separated azeotropically with water, and 50 g of toluene was added to the resulting residue, followed by cooling.

The, the crystals deposited were collected by filtration, followed by drying to obtain 26 g of 2-phenyl-1,3-propanediol (yield: 79.5%).

EXAMPLE 24

In 10 ml of tetrahydrofuran, 2.6 g of 2,2-dimethyl-1,3-dioxan-5-one was dissolved, and the solution was cooled to 10° C. Thereafter, a solution obtained by dissolving in 10 ml of tetrahydrofuran 3.8 g of phenyl magnesium bromide prepared from phenyl bromide was dropwise added thereto over a period of 3 hours. Subsequently, the mixture was stirred for 3 hours, and its temperature was raised to room temperature.

Gas chromatography was carried out to make sure that the charged starting 2,2-dimethyl-1,3-dioxan-5-one had disappeared.

Next, 50 ml of an aqueous 10% ammonium chloride solution was added to stop the reaction. The reaction product was extracted with ether and the solvent was removed, followed by distillation to obtain 2.71 g of the desired compound 5-hydroxy-5-phenyl-2,2-dimethyl-1,3-dioxane (yield: 65%).

The boiling point of the 5-hydroxy-5-phenyl-2,2-dimethyl- 1,3-dioxane obtained in the present Example is 142° C./2 Torr, and the results of $^1$H-NMR analysis (solvent: $CDCl_3$; chemical shift, δ) of the same are as shown in Table 8.

TABLE 8

| Results of $^1$H-NMR analysis ($CDCl_3$, δ) |
|---|
| 7.31–7.54(m, 5H) |
| 4.13(d, 2H, J=15Hz) |
| 4.02(d, 2H, J=15Hz) |
| 1.52(S, 3H) |
| 1.47(S, 3H) |

EXAMPLE 25

In 10 ml of tetrahydrofuran, 2.6 g of 2,2-dimethyl-1,3-dioxan-5-one was dissolved, and the solution was cooled to 10° C. Thereafter, a solution obtained by dissolving in 10 ml of tetrahydrofuran 3.8 g of phenyl magnesium bromide prepared from phenyl bromide was dropwise added thereto over a period of 3 hours. Subsequently, the mixture was stirred for 3 hours, and its temperature was raised to room temperature.

Gas chromatography was carried out to make sure that the charged starting 2,2-dimethyl-1,3-dioxan-5-one had disappeared.

Next, 1.73 g of acetyl chloride was dropwise added, further followed by stirring for 2 hours. Thereafter, water was added to stop the reaction. The reaction product was extracted with ether and the solvent was removed, followed by distillation to obtain 3.95 g of the desired compound 5-acetoxy-5-phenyl-2,2-dimethyl-1,3-dioxane (yield: 79%).

The boiling point of the 5-acetoxy-5-phenyl-2,2-dimethyl- 1,3-dioxane obtained in the present Example is 165° C./1.7 Torr, and the results of $^1$H-NMR analysis (solvent: $CDCl_3$; chemical shift, δ) of the same are as shown in Table 9.

TABLE 9

| Results of $^1$H-NMR analysis ($CDCl_3$, δ) |
|---|
| 7.31–7.51(m, 5H) |
| 4.13(d, 2H, J=12.0Hz) |

TABLE 9-continued

| Results of $^1$H-NMR analysis ($CDCl_3$, δ) |
|---|
| 4.06(d, 2H, J=12.0Hz) |
| 2.01(S, 3H) |
| 1.52(S, 3H) |
| 1.47(S, 3H) |

EXAMPLE 26

In 10 ml of toluene, 2.6 g of 2,2-dimethyl-1,3-dioxan-5-one was dissolved, and the solution was cooled to −10° C. Thereafter, a solution obtained by dissolving in 20 ml of toluene 1.77 g of phenyl lithium prepared from phenyl was dropwise added thereto over a period of 3 hours. Subsequently, the mixture was stirred for 3 hours, and its temperature was raised to room temperature.

Gas chromatography was carried out to make sure that the charged starting 2,2-dimethyl-1,3-dioxan-5-one had disappeared.

Next, 1.73 g of acetyl chloride was dropwise added, further followed by stirring for 2 hours. Thereafter, water was added to stop the reaction. The reaction product was extracted with ether and the solvent was removed, followed by distillation to obtain 2.92 g of the desired compound 5-acetoxy-5-phenyl-2,2-dimethyl-1,3-dioxane (yield: 74%).

EXAMPLE 27

In 20.0 g of isopropyl alcohol, 2.0 g of the 5-acetoxy-5-phenyl-2,2-dimethyl-1,3-dioxane obtained in Example 25 was dissolved, and 0.08 g of a 5% Pd/C catalyst was further added. Reaction was carried out at a hydrogen pressure of 5 $kg/cm^2$ at 50° C. for 12 hours.

After the reaction was completed, the catalyst Pd/C was removed and the isopropyl alcohol was further removed, followed by addition of 10 g of toluene and 10 g of 10% hydrochloric acid to carry out hydrolysis.

Thereafter, the aqueous layer was removed, further followed by crystallization from toluene to obtain 1.07 g of 2-phenyl-1,3-propanediol (yield: 88%), a precursor of felbamate having the action as an antiepileptic.

What is claimed is:

1. A process for producing the compound of Formula (1a)

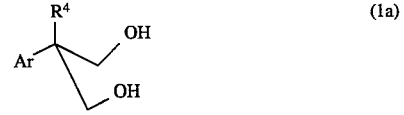

said process comprising the step of allowing a compound represented by Formula (5):

wherein Ar represents an aryl group and $R^4$ represents an alkoxy group having 1 to 10 carbon atoms; to react with formalin in the presence of a basic catalyst.

* * * * *